United States Patent [19]
Dittmar

[11] 3,970,668
[45] July 20, 1976

[54] DIALKYL 1,1'-(OPTIONALLY SUBSTITUTED HYDROCARBYLENEBISCARBAMOYL)-BIS(2-BENZIMIDAZOLECABAMATES)

[75] Inventor: Bruce Ivor Dittmar, Wilmington, Del.

[73] Assignee: E. I. Du Pont de Nemours and Company, Wilmington, Del.

[22] Filed: Feb. 25, 1972

[21] Appl. No.: 229,559

Related U.S. Application Data

[63] Continuation-in-part of Ser. No. 841,987, July 15, 1969, abandoned.

[52] U.S. Cl.................. 260/309.2; 260/268 BC; 260/453 A; 260/453 AP; 260/453 AL; 260/453 AR; 424/273
[51] Int. Cl.$^2$................................ C07D 235/32
[58] Field of Search............................ 260/309.2

[56] References Cited
UNITED STATES PATENTS
3,541,213  11/1970  Klopping.................. 260/309.2

Primary Examiner—Sherman D. Winters

[57] ABSTRACT

Dialkyl 1,1'-(hydrocarbylenebiscarbamoyl)bis(2-benzimidazolecarbamate) as fungicides and mite ovicides.

6 Claims, No Drawings

DIALKYL 1,1'-(OPTIONALLY SUBSTITUTED HYDROCARBYLENEBISCARBAMOYL)BIS(2-BENZIMIDAZOLECARBAMATES)

CROSS REFERENCE TO RELATED APPLICATION

This application is a continuation-in-part of copending application, Ser. No. 841,987, filed July 15, 1969, now abandoned.

BACKGROUND OF THE INVENTION

Various benzimidazolecarbamates have been found to have outstanding fungicidal activity. Examples of such compounds can be found in U.S. Pat. Nos. 2,933,502 and 2,933,504 and Belgian Pat. No. 698,071.

This invention relates to a novel group of dialkyl [1,1'-(optionally substituted hydrocarbylenebiscarbamoyl)-bis-2-benzimidazolecarbamates] and to methods of using these compounds to prevent or mitigate damage to plants and inanimate organic material by fungi and mites. Fungus mycelia are killed or prevented from developing further by the presence of one or more of the compounds, i.e., the compounds are fungicidal or fungistatic.

SUMMARY OF THE INVENTION

It has been found that outstanding fungicidal and mite ovicidal activity can be obtained by applying to the locus of infection and/or infestation the compounds represented by the following formula:

FORMULA I

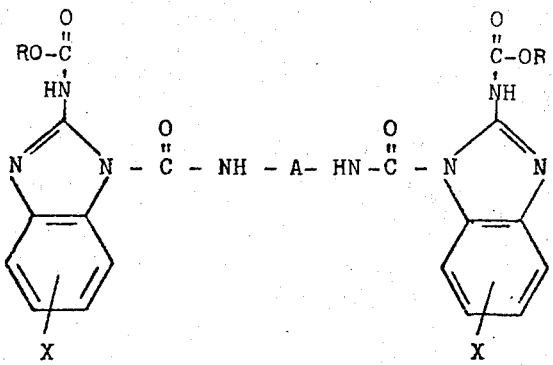

wherein
the R's can be the same or different and are methyl, ethyl, isopropyl or sec-butyl;
X is hydrogen, halogen, methyl or methoxy;
A is a difunctional group of 1 to 18 carbon atoms selected from
alkylene;
alkylene substituted by oxa, N-methylaza or thia;
alkenylene;
cycloalkylene cycloalkenylene;
bis(cyclohexylene)methylene;
alkylated cyclohexylene alkenylated alkylcyclohexylene;
alkyleneated cyclohexylene;
alkylated cycloalkylene substituted by oxyalkylene or methylene;
N-alkyleneated azacyclohexane;
bicycloalkylene;
phenylene;
methylated phenylene; and
bis(phenylene)methylene.

Preferred because of ease of manufacture are those compounds where A is hydrocarbylene.

Preferred because of their biological activity are those compounds within Formula I wherein R is methyl and X is hydrogen.

Particularly preferred are the following compounds:
methyl 1-{5-[2-(methoxycarbonylamino)-1-benzimidazolecarbonylamine]-1,3,3-trimethylcyclohexylmethylcarbamoyl}-2-benzimidazolecarbamate,

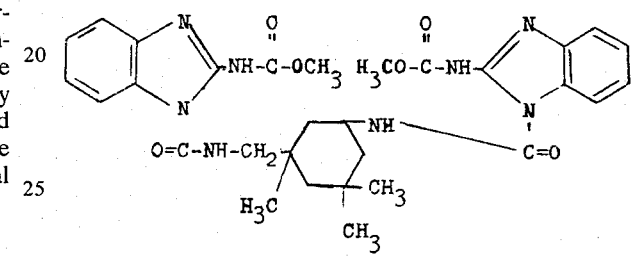

dimethyl 1,1'-(2,2,4-trimethylhexamethylenedicarbamoyl)bis(2-benzimidazolecarbamate),

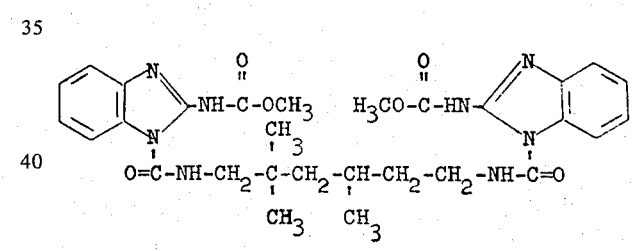

dimethyl 1,1'-(4-methyl-m-phenylenedicarbamoyl)-bis(2-benzimidazolecarbamate),

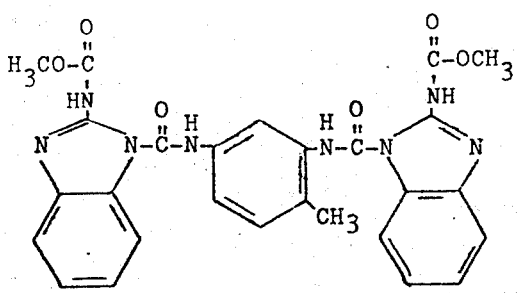

dimethyl 1,1'-(p-phenylenedicarbamoyl)bis(2-benzimidazolecarbamate),

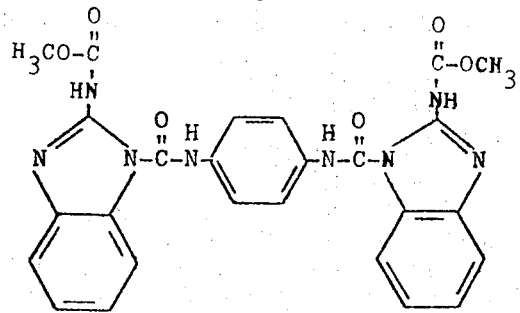

and dimethyl 1,1'[methylenedi-(p-phenylcarbamoyl)](2-benzimidazolecarbamate)

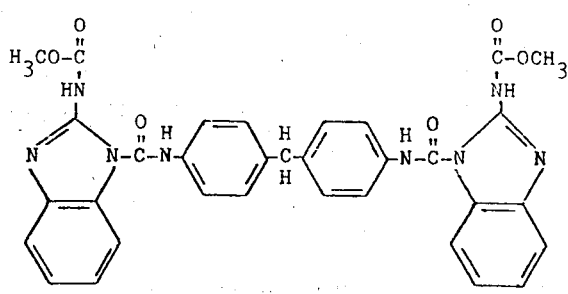

DETAILED DESCRIPTION OF THE INVENTION

I have found that if two molecules of an alkyl 2-benzimidazolecarbamate (II) are linked together with a diisocyanate, (III), the resulting compounds (I) of this invention are active fungicides and mite ovicides; this reaction can be illustrated as follows:

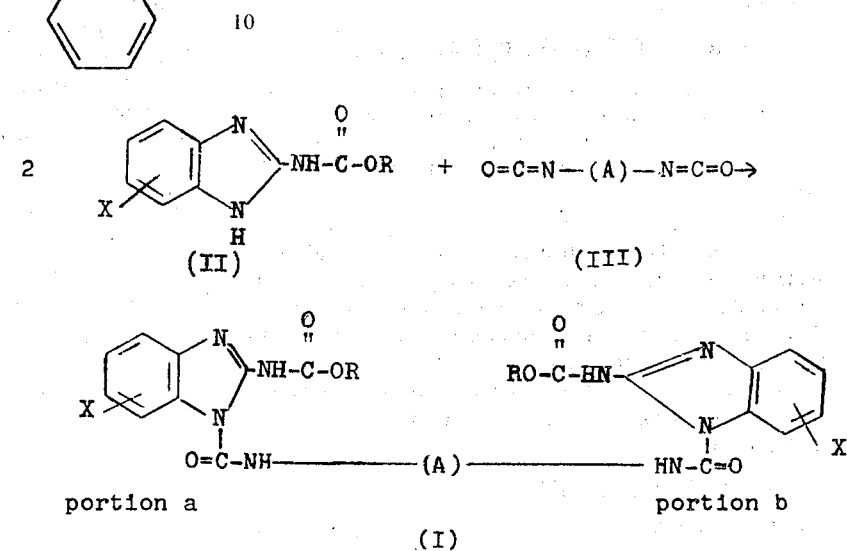

X, R, and A are as previously defined.

When the two molecules of the alkyl 2-benzimidazolecarbamate (II) are the same, portions a and b of the product (I) are the same. However, the two molecules need not be the same, thus portions a and b of the the product (I) can be different. I have also found that a large number of diisocyanates (III) are useful in the preparation of the product (I), consequently a large number of linking groups A are possible.

PREPARATION PROCEDURES

The compounds of this invention wherein the two R groups are the same can be prepared by reacting 2 moles of an alkyl 2-benzimidazolecarbamate (II) with an optionally substituted hydrocarbylene diisocyanate (III), as shown below.

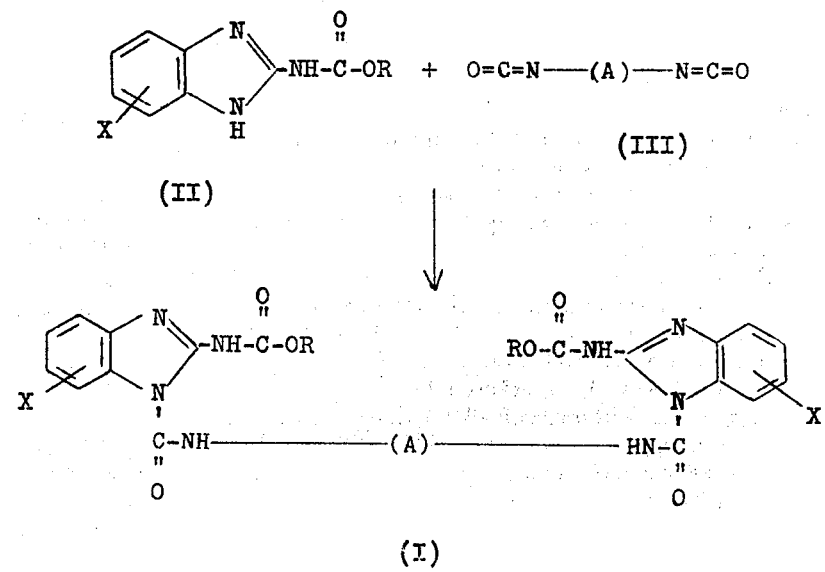

The compounds I wherein the two R groups are different can be prepared by the reaction of a mole of an alkyl 2-benzimidazolecarbamate (II) with a mole of an optionally substituted hydrocarbylene diisocyanate (III), followed by the reaction of the intermediate (IV) with an alkyl 2-benzimidazolecarbamate (II) which differs from the first-used component II in that the R group or X substituent are different. Compounds I in which the R groups and X substituents are the same are preferred because of greater ease of preparation. The definitions of R, X, and A are the same as previously indicated.

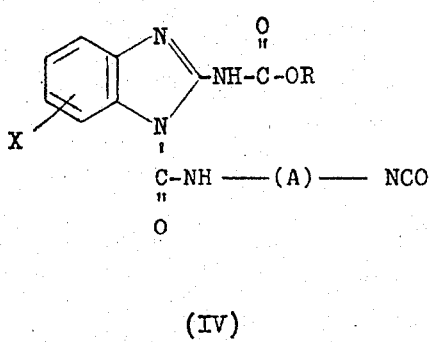

(IV)

The starting alkyl 2-benzimidazolecarbamates (II) can be prepared by methods known to the art, e.g. by a three-reaction sequence taught in U.S. Pat. No. 3,010,968.

Hydrocarbylene diisocyanates may be prepared by reacting the corresponding diamine with phosgene [Siefken, Ann., 562, 76 (1948)].

The following examples serve to illustrate the general method of preparation of the compounds of this invention. Unless otherwise stated, all parts are by weight.

EXAMPLE 1

Preparation of Dimethyl 1,1'-(Hexamethylenedicarbamoyl)bis(2-benzimidazolecarbamate)

To a stirred mixture of methyl 2-benzimidazolecarbamate (19.1 parts) and triethylenediamine (0.1 parts) in acetone (300 parts) was slowly added hexamethylene diisocyanate (8.4 parts). The reaction was mildly exothermic and the mixture became very thick. The reaction mixture was stirred at room temperature overnight, and the solid was collected by filtation. The product, dimethyl 1,1'-(hexamethylenedicarbamoyl)-bis(2-benzimidazolecarbamate), 27.1 parts was washed with acetone and dried in a vacuum oven at room temperature. It exhibited melting point 322°–324°C. (dec.).

Analysis Calcd. for $C_{26}H_{30}N_8O_6$: C, 56.85; H, 5.50; N, 20.20%. Analysis Found: C, 56.69; H, 5.54; N, 19.92%.

EXAMPLE 2

Preparation of Methyl 1-{5-[2-(methoxycarbonylamino)-1-benzimidazolyl-carbonylamino]-1,3,3-trimethylcyclohexylmethylcarbamoyl}-2-benzimidazolecarbamate To a stirred mixture of methyl 2-benzimidazolecarbamate (19.1 parts) and triethylenediamine (0.1 part) in chloroform (300 parts) was slowly added 5-isocyanato-1-(isocyanatomethyl)-1,3,3-trimethylcyclohexane (11.1 parts). The reaction mixture was stirred at room temperature overnight, filtered and the solvent removed from the filtrate under reduced pressure. The residue from the filtrate was triturated with hexane and the product methyl 1-{5-[2-(methoxycarbonylamino)-1-benzimidazolylcarbonylamino]-1,3,3-trimethylcyclohexylmethylcarbamoyl}-2- benzimidazolecarbamate (28.5 parts) was collected by filtration. It exhibited a melting point of 82°–83°C.

EXAMPLE 3

Preparation of Dimethyl 1,1'-(2,2,4-trimethylhexamethylenedicarbamoyl)-bis(2-benzimidazolecarbamate)

To a stirred mixture of methyl 2-benzimidazolecarbamate (19.1 parts) and triethylenediamine (0.1 part) in chloroform (300 parts) was slowly added 2,2,4-trimethylhexamethylene diisocyanate. The reaction mixture was stirred at room temperature overnight, filtered, and the solvent removed from the filtrate under reduced pressure. The solid from the filtrate was ground in hexane and the product dimethyl 1,1'-(2,2,4-trimethylhexamethylenedicarbamoyl)bis(2-benzimidazolecarbamate) (27 parts) was collected by filtration. It exhibited a melting point of 78°–80°C.

EXAMPLE 4

Preparation of Methyl 1-{6-[2-(Isopropoxycarbonylamino)-1-benzimidazolylcarbonylamino]hexamethylenecarbamoyl}-2-benzimidazolecarbamate To a stirred solution of hexamethylene diisocyanate (16.8 parts) and triethylenediamine (0.1 part) (600 parts) is slowly added isopropyl 2-benzimidazolecarbamate (21.9 parts). The reaction mixture is stirred at room temperature for 1 hour, then methyl 2-benzimidazolecarbamate (19.1 parts) is slowly added to the reaction. The reaction mixture is stirred at room temperature overnight, filtered and the solvent removed from the filtrate under reduced pressure. The residue from the filtrate is triturated with hexane and the product methyl 1-{6-[2-(isopropoxycarbonylamino)-1-benzimidazolylcarbonylamine]hexamethylenecarbamoyl}-2-benzimidazolecarbamate is collected by filtration.

EXAMPLE 5

Preparation of Dimethyl 1,1'-(4-methyl-m-phenylenedicarbamoyl)bis(2-benzimidazolecarbamate)

To a stirred mixture of methyl 2-benzimidazolecarbamate (19.1 parts) and triethylamine (0.1 part) in methyl ethyl ketone (300 parts) was slowly added 4-methyl-m-phenylene diisocyanate (8.7 parts) in methyl ethyl ketone (20 parts. The reaction mixture was stirred at room temperature for 1 hour, filtered to recover the solid phase. The solid was air dried overnight. The product dimethyl 1,1'-(4-methyl-m-phenylenedicarbamoyl)bis(2-benzimidazolecarbamate) (27.3 parts) exibited a melting point of 203°–205°C.

EXAMPLE 6

Preparation of Dimethyl 1,1'-(p-phenylenedicarbamoyl)bis(2-benzimidazolecarbamate To a stirred mixture of methyl 2-benzimidazole carbamate (19.1 parts) and triethylamine (0.1 part) in methyl ethyl ketone (300 parts) was slowly added p-phenylene diisocyanate (8 parts) in methyl ether ketone (20 parts). The reaction mixture was stirred at room temperature overnight. The solid was recovered from the reaction mixture by filtration and air dried. The product dimethyl 1,1'-(p-phenylenedicarbamoyl)bis(2-benzimidazolecarbamate) (26 parts) exihibited a melting point of 350°C.

EXAMPLE 7

Preparation of Dimethyl 1,1'-[methylenedi(p-phenylcarbamoyl)]bis(2-benzimidazolecarbamate)

To a stirred mixture of methyl 2 benzimidazolecarbamate (19.1 parts) and triethylamine (0.1 part) in chloroform (300 parts) was slowly added methylenedi(p-phenylisocyanate) (12.5 )parts). The reaction mixture was stirred at room temperature overnight. The solid was recovered from the reaction mixture by filtration and air dried. The product dimethyl 1,1'-[methylenedi(p-phenylcarbamoyl)]bis(2-benzimidazolecarbamate) 30 parts) exhibited a melting point of 330°–334°C.

EXAMPLE 8

The following compounds can be prepared by following the procedure outlined in Example 3 in which methyl 2-benzimidazolecarbamate and 2,2,4-trimethylhexamethylene diisocyanate are replaced by the indicated alkyl 2-benzimidazolecarbamate and optionally substituted hydrocarbylene diisocyanate, respectively.

| Sample | Dialkyl [1,1'-(Optionally Substituted Hydrocarbylenebiscarbamoyl)bis(2-benzimidazolecarbamate) | Alkyl 2-benzimidazole-carbamate | Optionally Substituted Hydrocarbylene Diisocyanate |
| --- | --- | --- | --- |
| 1 | dimethyl 1,1'-(dodecamethylenedicarbamoyl)bis(2-benzimidazolecarbamate) | methyl 2-benzimidazole-carbamate | dodecamethylene diisocyanate |
| 2 | dimethyl 1,1'-(ethylenedicarbamoyl)bis(2-benzimidazolecarbamate) | methyl 2-benzimidazole-carbamate | ethylene diisocyanate |
| 3 | dimethyl 1,1'-(1,1-dimethylethylenedicarbamoyl)bis(2-benzimidazolecarbamate) | methyl 2-benzimidazole-carbamate | 1,1-dimethylethylene diisocyanate |
| 4 | dimethyl 1,1'-(2,2-dimethyltrimethylenedicarbamoyl)bis(2-benzimidazolecarbamate) | methyl 2-benzimidazole-carbamate | 2,2-dimethyltrimethylene diisocyanate |
| 5 | dimethyl 1,1'-(1,4-cyclohexylenedicarbamoyl)bis(2-benzimidazolecarbamate) | methyl 2-benzimidazole-carbamate | 1,4-cyclohexylene diisocyanate |
| 6 | dimethyl 1,1'-(1,4-cyclohexylenedimethylenedicarbamoyl)bis(2-benzimidazolecarbamate) | methyl 2-benzimidazole-carbamate | 1,4-cyclohexylenedimethylene diisocyanate |
| 7 | diisopropyl 1,1'-(1-3-cyclohexylenedicarbamoyl)bis(2-benzimidazolecarbamate) | isopropyl 2-benzimidazole-carbamate | 1,3-cyclohexylene diisocyanate |
| 8 | dimethyl 1,1'-[methylenebis(4-cyclohexylcarbamoyl)]bis(2-benzimidazolecarbamate) | methyl 2-benzimidazole-carbamate | methylenebis(4-cyclohexylisocyanate) |
| 9 | dimethyl 1,1'-[bis(1,4-cyclohexylene)dicarbamoyl]bis(2-benzimidazolecarbamate) | methyl 2-benzimidazole-carbamate | bis-(1,4-cyclohexylene) diisocyanate |
| 10 | dimethyl 1,1'-(decahydro-1,5-naphthylenedicarbamoyl]bis(2-benzimidazolecarbamate) | methyl 2-benzimidazole-carbamate | decahydro-1,5-naphthylene diisocyanate |
| 11 | dimethyl 1,1'-(2-buten-1,4-ylenedicarbamoyl)bis(2-benzimidazolecarbamate) | methyl 2-benzimidazole-carbamate | 2-buten-1,4-ylene diisocyanate |
| 12 | dimethyl 1,1'-(tetramethylenedicarbamoyl)bis(2-benzimidazolecarbamate) | methyl 2-benzimidazole-carbamate | tetramethylene diisocyanate |
| 13 | dimethyl 1,1'-(octamethylenedicarbamoyl)bis(2-benzimidazolecarbamate) | methyl 2-benzimidazole-carbamate | octamethylene diisocyanate |
| 14 | dimethyl 1,1'-(1,2-dimethylethylenedicarbamoyl)bis(2-benzimidazolecarbamate) | methyl 2-benzimidazole-carbamate | 1,2-dimethylethylene diisocyanate |
| 15 | dimethyl 1,1'-(2-methyltetramethylenedicarbamoyl)bis(2-benzimidazolecarbamate) | methyl 2-benzimidazole-carbamate | 2-methyltetramethylene diisocyanate |
| 16 | dimethyl 1,1'-(1,3-cyclohexylene dimethylenecarbamoyl)bis(2-benzimidazolecarbamate) | methyl 2-benzimidazole-carbamate | 1,3-cyclohexylenedimethylene diisocyanate |
| 17 | methyl 1-{4-[2-(methoxycarbonylamino)-1-benzimidazolylcarbonylamino]-1-methylcyclohexylmethylethyl}2-benzimidazole carbamate | methyl 2-benzimidazole-carbamate | 1-methyl-1-isocyanato-4-(1-isocyanate-1-methylethyl)cyclohexane |
| 18 | dimethyl 1,1'-(1,2-cyclobutylenedicarbamoyl)bis(2-benzimidazolecarbamate) | methyl 2-benzimidazole-carbamate | 1,2-cyclobutylene diisocyanate |
| 19 | dimethyl 1,1'-(1,2-cyclohexylenedicarbamoyl)bis(2-benzimidazole- | methyl 2-benzimidazole-carbamate | 1,2-cyclohexylene diisocyanate |

-continued

| Sample | Dialkyl [1,1'-(Optionally Substituted Hydrocarbylenebiscarbamoyl)bis(2-benzimidazolecarbamate) | Alkyl 2-benzimidazole-carbamate | Optionally Substituted Hydrocarbylene Diisocyanate |
|---|---|---|---|
| 20 | dimethyl 1,1'-(isopropylidenebis-1,4-cyclohexylenedicarbamoyl)bis(2-benzimidazolecarbamate) | methyl 2-benzimidazole-carbamate | isopropylidenebis(1,4-cyclohexylene) diisocyanate |
| 21 | dimethyl 1,1'-(oxydiethylenedicarbamoyl)bis(2-benzimidazolecarbamate) | methyl 2-benzimidazole-carbamate | oxydiethylene diisocyanate |
| 22 | dimethyl 1,1'-(1-methylethylenedicarbamoyl)bis(2-benzimidazolecarbamate) | ethyl 2-benzimidazole-carbamate | 1-methylethylene diisocyanate |
| 23 | dimethyl 1,1'-(1,4-piperazinylenebistrimethylenedicarbamoyl)bis(2-benzimidazolecarbamate) | methyl 2-benzimidazole-carbamate | 1,4-piperazinylenebistrimethylene diisocyanate |
| 24 | dimethyl 1,1'-(2,2,4,4-tetramethyl-1,3-cyclobutylenedicarbamoyl)bis(2-benzimidazolecarbamate | methyl 2-benzimidazole-carbamate | 2,2,4,4-tetramethyl-1,3-cyclohexylene diisocyanate |
| 25 | dimethyl 1,1'-(2-methyl-1,3-cyclohexylenedicarbamoyl)bis(2-benzimidazolecarbamate) | methyl 2-benzimidazole-carbamate | 2-methyl-1,3-cyclohexylene diisocyanate |
| 26 | dimethyl 1,1'-[methyliminodi(trimethylene)dicarbamoyl]bis(2-benzimidazolecarbamate) | methyl 2-benzimidazole-carbamate | methyliminodi(trimethylene) diisocyanate |
| 27 | dimethyl 1,1'-[2,2,4,4-tetramethyl-1,3-cyclobutylenebis(oxytrimethylene)dicarbamoyl]bis(2-benzimidazolecarbamate) | methyl 2-benzimidazole-carbamate | 2,2,4,4-tetramethyl-1,3-cyclobutylene-bisoxytrimethylene diisocyanate |
| 28 | dimethyl 1,1'-(2-methyl-1,5-cyclohexylenedicarbamoyl)bis(2-benzimidazolecarbamate) | methyl 2-benzimidazole-carbamate | 2-methyl-1,5-cyclohexylene diisocyanate |
| 29 | diethyl 1,1'-(3-methyl-1-4-cyclohexylenedicarbamoyl)bis(2-benzimidazolecarbamate) | ethyl 2-benzimidazole-carbamate | 3-methyl-1,4-cyclohexylene diisocyanate |
| 30 | dimethyl 1,1'-(octadecamethylenedicarbamoyl)bis(2-benzimidazolecarbamate. | methyl 2-benzimidazole-carbamate | octadecamethylene diisocyanate |
| 31 | dimethyl 1,1'(hexamethylenedicarbamoyl)bis(4-chloro-2-benzimidazolecarbamate) | methyl 4-chloro-2-benzimidazolecarbamate | hexamethylene diisocyanate |
| 32 | dimethyl 1,1'-[methylenebis(1,4-cyclohexylene)dicarbamoyl]bis(5-fluoro-2-benzimidazolecarbamate) | methyl 5-fluoro-2-benzimidazolecarbamate | methylenebis(1,4-cyclohexylene) diisocyanate |
| 33 | dimethyl 1,1'-(1,3-cyclohexylenedicarbamoyl)bis(4-bromo-2-benzimidazolecarbamate) | methyl 4-bromo-2-benzimidazolecarbamate | 1,3-cyclohexylene diisocyanate |
| 34 | dimethyl 1,1'-(dodecamethylenedicarbamoyl)bis(5-iodo-2-benzimidazolecarbamate) | methyl 5-iodo-2-benzimidazolecarbamate | dodecamethylene diisocyanate |
| 35 | dimethyl 1,1'-(1,4-cyclohexylenedicarbamoyl)bis(4-methyl-2-benzimidazolecarbamate) | methyl 4-methyl-2-benzimidazolecarbamate | 1,4-cyclohexylene diisocyanate |
| 36 | dimethyl 1,1'-(tetramethylenedicarbamoyl)bis(6-methoxy-2-benzimidazolecarbamate) | methyl 6-methoxy-2-benzimidazolecarbamate | tetramethylene diisocyanate |
| 37 | dimethyl 1,1'-(hexamethylenedicarbamoyl)bis(5-methyl-2-benzimidazolecarbamate) | methyl 5-methyl-2-benzimidazolecarbamate | hexamethylene diisocyanate |
| 38 | dimethyl 1,1'-[bis(1,4-cyclohexylenedicarbamoyl)]bis(4-nitro-2-benzimidazolecarbamate) | methyl 4-nitro-2-benzimidazolecarbamate | bis(1,4-cyclohexylene) diisocyanate |
| 39 | dimethyl 1,1'-(p-phenylenedimethylenedicarbamoyl)bis(2-benzimidazolecarbamate) | methyl 2-benzimidazole-carbamate | p-phenylenedimethylene diisocyanate |
| 40 | dimethyl 1,1'-(m-phenylenedimethylenedicarbamoyl)bis(2-benzimidazolecarbamate) | methyl 2-benzimidazole-carbamate | m-phenylenedimethylene diisocyanate |
| 41 | dimethyl 1,1'-(o-phenylenedimethylenedicarbamoyl)bis(2-benzimidazolecarbamate | methyl 2-benzimidazole-carbamate | o-phenylenedimethylene diisocyanate |
| 42 | dimethyl 1,1'-[(4-methyl-m-phenylene)-dimethylenedicarbamoyl]bis(2-benzimidazolecarbamate | methyl 2-benzimidazole-carbamate | 4-methyl-m-phenylenedimethylene diisocyanate |
| 43 | dimethyl 1,1'-(vinylenedicarbamoyl)-bis(2-benzimidazolecarbamate) | methyl 2-benzimidazole-carbamate | vinylene diisocyanate |
| 44 | diethyl 1,1'-(hexamethylenedicarbamoyl)bis(2-benzimidazolecarbamate) | ethyl 2-benzimidazole-carbamate | hexamethylene diisocyanate |
| 45 | diisopropyl 1,1'-(hexamethylenedicarbamoyl)bis(2-benzimidazolecarbamate) | isopropyl 2-benzimidazole-carbamate | hexamethylene diisocyanate |
| 46 | di-sec-butyl 1,1'-(hexamethylenedicarbamoyl)bis(2-benzimidazolecarbamate) | sec-butyl 2-benzimidazole-carbamate | hexamethylene diisocyanate |
| 61 | dimethyl 1,1'-(2-cyclopenten-1,4-ylenedicarbamoyl)bis(2-benzimidazolecarbamate) | methyl 2-benzimidazole-carbamate | 2-cyclopenten-1,4-ylene diisocyanate |
| 62 | dimethyl 1,1'-(2-cyclododec-1,4-ylenedicarbamoyl)bis(2-benzimidazolecarbamate) | methyl 2-benzimidazole-carbamate | 2-cyclododecen-1,4-ylene diisocyanate |
| 63 | dimethyl 1,1'-(1,4-cyclododecylenedi- | methyl 2-benzimidazole- | 1,4-cyclododecylene diisocyanate |

| Sample | Dialkyl [1,1'-(Optionally Substituted Hydrocarbylenebiscarbamoyl)bis(2-benzimidazolecarbamate) | Alkyl 2-benzimidazole-carbamate | Optionally Substituted Hydrocarbylene Diisocyanate |
|---|---|---|---|
| | carbamoyl)bis(2-benzimidazole-carbamate) | carbamate | |
| 64 | dimethyl 1,1'-(m-phenylenedicarbamoyl)bis(2-benzimidazole-carbamate) | methyl 2-benzimidazole-carbamate | m-phenylene diisocyanate |
| 65 | dimethyl 1,1'-(2-methyl-m-phenylene-dicarbamoyl)bis(2-benzimidazole-carbamate) | methyl 2-benzimidazole-carbamate | 2-methyl-m-phenylene diisocyanate |

As mentioned previously, it has been found that the compounds of Formula I possess outstanding fungicidal and mite ovicidal activity when employed to prevent or mitigate damage to plants and inanimate organic materials. A further aspect of this invention involves methods which when used in conjunction with the compounds of Formula I, result in advances in mite and fungus control of great practical importance. The paragraphs which follow describe in more detail the utility of this invention.

The compounds of the invention control a wide variety of fungus diseases of foliage, fruit, stems and roots of growing plants without damage to the host. Fruits, tubers, bulbs, roots, seeds and other plant parts harvested for food, animal feed or for other purposes are protected from fungus deterioration during processing, distribution and storage. Seeds, tubers, cuttings and other plant propagation materials are protected from fungus attack during handling and storage, as well as in the soil after planting. Wood, fabric, fiber board, paper and other industrial materials are protected from unsightly stain and destructive decay caused by fungi. Luggage, shoes, shower curtains, carpets, mats, clothing and other useful household, public or industrial items are protected from rot, fungus stains and mold growth. Painted surfaces are protected from stain and discoloration by incorporation of a compound of this invention in the paint formulation.

The many fungi against which the compounds of this invention are active may be represented by, but is not intended to be limited to, the following: *Venturia inaequalis*, which causes apple scab; *Podosphaera leucotricha*, which causes powdery mildew on apple; *Uromyces phaseoli*, which causes bean rust; *Cercospora apii*, which causes early blight of celery; *Cercospora beticola*, which causes leaf spot of sugar beets; *Sclerotinia sclerotiorum*, which causes rot of vegetable crops, such as lettuce, beans, carrots, and celery; *Colletotrichum* spp., which cause anthracnose of fruits and vegetables, such as beans, tomatoes and coffee; *Septoria apii*, which causes late blight of celery; *Cercospora musae*, which causes Sigotoka disease of banana; *Piricularia* sp., which causes Johnson spot on banana; *Erysiphe cichoracearum*, which causes powdery mildew on cantaloupe and other cucurbit crops; *Penicillium digitatum*, Phomopsis spp., and *Diplodia natalensis*, which cause fruit rots on citrus; *Ceratostomella ulmi*, which causes Dutch elm disease; *Sphaerotheca humuli*, which causes powder mildew on roses; *Diplocarpon rosae*, which causes black spot on roses; *Ramularia* sp., which causes leaf spots on ornamental plants; *Botrytis cinerea*, which causes blossom and fruit rots of ornamentals, fruits and vegetables; *Uncinula necator*, which causes powdery mildew on grapes; *Guignardia bidwellii*, which causes grape black rot; *Melonconium fuligineum*, which causes white rot of grapes; *Coccomyces hiemalis*, which causes cherry leaf spot; *Cytospora* sp., which cause cankers of trees; *Cladosporium carpophilum*, which causes peach scab; *Fusicladium effusum*, which causes pecan scab; *Erysiphe graminis*, which causes powder mildew on cereals; *Monolinia (Sclerotinia) laxa* and *M. fructicola*, which cause brown rot of stone fruits, such as peaches, cherries, and apricots, *Pseudopeziza ribes*, which causes leaf spot on gooseberry; *Piricularia oryzae*, which causes rice blast; *Puccinia glumarum* and *P. coronata* which cause leaf rusts of wheat, oats and grasses, respectively; *Puccinia graminis tritici*, which causes stem rust of wheat; *Claviceps purpurea*, which causes ergot of rye and grasses; *Aspergillus niger*, which causes bottom boll rot as well as decay following wounding in many plant tissues; *Aspergillus flavus*, which causes mold growth in peanuts, as well as on other food and field materials; *Aspergillus terreus*, which is common in soil and attacks vegetable matter; *Tilletia caries* and other Tilletia species, which cause common bunt of wheat; *Ustilago tritici*, *Ustilago nigra*, *Ustilago avena* (and other *Ustilago* species), which cause loose smut of wheat, barley, and oats, respectively; *Urocystis tritici* and other Urocystis species, which cause loose smut of wheat; *Sphacelotheca sorghi*, which causes covered smut of sorghum; *Ustilago hordei* and *Ustilago kolleri*, which cause covered smut of barley and oats, respectively; *Pithomyces chartorum*, which is present in turf, pastures, and other grassy areas and is known to have several secondary effects; *Gloeodes pomigena*, which causes sooty blotch on apples; *Physalospora obtusa*, which causes black rot on apples; *Microthyriella rubi*, which causes flyspeck on apples; various species of Rhizoctonia, Fusarium and Verticillium present in soil and attacking the roots or other underground parts and the vascular system of a variety of plants; various species of Penicillium growing on such things as fabric, fiber board, leather goods and paint; species of Myrothecium attacking such items as shower curtains, carpets, mats and clothing.

The mite ovicidal action of the compounds of this invention is useful in preventing the development of damaging populations of mites or in causing the gradual reduction of existing populations. The movement of mites is limited. Thus, an increase in population or the continuation of a high population in a particular locus depends largely upon the hatching of eggs laid in that locus.

Mite eggs do not hatch to produce living young if these eggs are treated with one of these compounds, or if they are laid on a surface containing one of these compounds. Further, the eggs will not hatch if they are laid by a female mite that has been in contact with one of these compounds, or are laid by a female mite that is ingesting or has recently ingested food such as plant juices containing one of these compounds. This interference with the hatching of eggs prevents the population from increasing significantly beyond that present at the time of treatment. Also, this ovidical action, along with the high natural mortality of adults, can largely eliminate mites from an already infested area over a relatively short period of time. Further, as long as the compounds are present on the surface the mites occupy or remain in their food supply, new populations cannot develop.

Many species of mites which cause damage to fruits, field crops, vegetables, and ornamentals under a wide variety of circumstances, are controlled by the compounds and methods of this invention. The extent of the practical utility of the mite control obtained is represented by, but is not intended to be limited to, the following listing of specific susceptible mites along with the types of damage that they can cause: *Panonychus ulmi* (European red mite) and *Tetranychus telarius* (two-spotted mite) which are commonly called "orchard mites"; these mites attack a great many deciduous tree fruits including apples, pears, cherries, plums and peaches; *Tetranychus atlanticus* (Atlantic or strawberry mite), *T. cinnabarinus* (carmine spider mite) and *T. pacificus* (Pacific mite); these mites attack cotton and numerous other crop plants; *Paratetranychus citri* (citrus red mite) and others which attack citrus; *Phyllocuptruta sleivora* which causes citrus rust; *Bryobia praetiosa* (clover mite) which attacks clover, alfalfa and other crops; *Phyllosoptruta oleivora*, the citrus rust mite; *Aceria neocynodomis* which attacks grasses and other plants; *Tyrophagus lintneri* which is a serious pest in stored foods and on cultivated mushrooms and *Lepidoglyphus destructor* which injures Kentucky bluegrass seed in storage.

The compounds of this invention when applied by certain of the methods of this invention enter and move freely within plants, i.e., they are systemic. Thus both fungi and mites can be controlled in plants in parts well removed from the point of application. In view of this activity the compounds can be applied to seeds; thus the treatment of cucumber seeds with a few grams per 50 kilograms of seed of a compound of this invention provides control of powdery mildew (*Erysiphe cichoracearum*) and spider mites such as *Tetranychus urticae* on the resulting plants for periods in excess of 40 days. Applications to soil also provides control of certain foliage diseases and mites on plants growing in the treated soil. Spray or dust treatments of plant foliage and stems impart protection against both fungi and mites to other parts of the plant not actually sprayed and to new foliage developing later.

There are important practical advantages associated with the use of an effective systemic pesticide. Thus successful application to seed as described above, results in great savings in chemical and application costs. Soil applications which effectively protect entire plants for an extended period also represent similar savings. Distribution within the plant following foliage treatment eliminates the need for frequent retreatment to protect rapidly growing tissue. Also, materials within the plant are not subject to removal by rainfall. Similarly, movement or translocation of the chemical within the plant can provide protection to those parts of the plant that may not have been covered by the original spray application. This is of particular importance with plants of dense growth character resisting the intrusion of the spray and also to tall plants, such as shade trees, where the spray will not reach to the top.

An additional valuable characteristic of the compounds of this invention is their ability to prevent the spread or to kill fungus infection already established within a plant, i.e. they are curative. Thus, the compounds need not be applied until after conditions develop which permit the actual initiation of fungus attack. This means that, under some circumstances, it is possible to avoid applying any chemical during the entire life of the crop. In other cases, only a part of the normal full schedule of pesticide is required.

Therefore great savings both in chemical cost and application labor are possible with compounds capable of systemic and curative performance. Another saving is afforded by the compounds of this invention through the fact that both fungi and mites are controlled by applications of a single chemical.

The compounds of this invention provide protection from damage caused by fungi, mites or both when applied to the proper locus by the methods described hereinafter and at a sufficient rate to exert the desired fungicidal and mite ovicidal effect. They are especially suited for the protection of living plants such as fruit-bearing trees, nut-bearing trees, ornamental trees, forest trees, vegetable crops, horticultural crops (including ornamentals, small fruits and berries), fiber crops, grain and seed crops, sugarcane, sugar beets, pineapple, forage and hay crops, beans, peas, soybeans, peanuts, potatoes, sweet potatoes, tobacco, hops, turf and pasture.

Living plants may be protected from fungi and mites by applying one or more of the compounds of this invention to the soil in which they are growing or in which they may subsequently be seeded or planted; or to seeds, tubers, bulbs or other plant reproductive parts prior to planting; as well as to foliage, stems and fruit of the living plant. Living plants can also be protected by dipping the root system or physically injecting the chemical or chemicals into roots or stems.

Soil applications are made from dusts, granules, pellets, slurries or solution. Preferred rates for application of the compounds of this invention to soil in which plants are or will be growing range from 0.01 to 500 parts per million by weight of the soil in which the roots are or will be growing. More preferred use rates are in the range of 0.1 to 50 parts per million, and the most preferred rates are in the range of 0.25 to 25 parts per million.

Preferred rates for application to seeds, tubers, bulbs or other plant reproductive parts, range from 0.03 to 6000 grams of active compound of this invention per 50 kilograms of planting material treated. More preferred rates are in the range of 0.3 to 3000 grams of active compound per 50 kilograms. The most preferred rates are in the range of 2.8 to 1500 grams per 50 kilograms. Applications are made from dusts, slurries or solutions. Such treatments protect the treated parts themselves from damage due to fungi, mites, or both, and in addition, impart extended protection against both types of pests to the resulting new plants.

Preferred rates for application of the compounds of this invention to foliage, stems and fruit of living plants range from 0.012 to 60 kilograms of active ingredient per hectare. More preferred rates are in the range of 0.025 to 30 kilograms per hectare and the most preferred rates are in the range of 0.05 to 15 kilograms per hectare. The optimum amount within this range depends upon a number of variables which are well known to those skilled in the art of plant protection.

These variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries or solutions.

Preferred rates for dip applications to roots of living plants are in the range of 0.5 to 18,000 grams of active ingredient per 380 liters of water or other liquid carrier. More preferred rates are in the range of 4.5 to 9,000 grams per 380 liters and the most preferred rates are in the range of 45 to 4500 grams per 380 liters.

Preferred rates for injection into the roots or stems of living plants are in the range of 0.01 to 10,000 parts per million of water or other liquid carrier. More preferred rates are in the range of 0.1 to 5,000 parts per million. The most preferred rates are in the range of 1 to 1,000 parts per million.

Plant parts such as fruits, tubers, bulbs, foliage roots and the like, harvested for food or feed, are protected from decay and other deterioration caused by fungi or mites during processing, distribution and storage by treatment with an active compound of this invention. The plant parts to be so protected can be dipped in a liquid bath containing the active ingredient, dusted with a finely divided preparation of the active ingredient, sprayed, misted with an aerosol containing the compound, or enclosed in wrapping or packing materials impregnated with the active compound.

If a liquid bath is used, it can contain an amount of the active ingredient in the range of 1 to 5,000 parts per million of the weight of the fluid. A more preferred range for the bath is 5 to 2,500 parts per million, and the most preferred range is 10 to 1,000 parts per million.

Dusts as well as wrapping or packing materials used for this type of application can contain 0.001 to 1.0% of the active ingredient. More preferred rates are in the range of 0.01 to 0.5% and the most preferred rates are in the range of 0.002 to 0.25%.

Wood, leather, fabric, fiber board, paper and other industrial materials of an organic nature can be protected from decomposition or discoloration by fungi and infestation by mites by coating, incorporating or impregnating with an effective amount of one or more of the compounds of this invention. The coating can be accomplished by dipping, spraying, flooding, misting (as with an aerosol) or dusting the material to be protected with a suitable composition containing the active ingredient. The preferred use rates for the active ingredient in the treating preparation actually applied to the material to be protected are in the range of 0.025 to 95% by weight. More preferred rates are in the range of 0.05 to 50%, with the most preferred rates being in the range of 0.1 to 25%.

Where incorporation or impregnation procedures are to be employed, use rates may be expressed in terms of the amount of active ingredient introduced into the material to be protected. The preferred use rates for these types of applications are in the range of 0.001 to 30 percent by weight of active ingredient in the final product. More preferred rates are in the range of 0.005 to 15% with the most preferred rates being in the range of 0.01 to 7%.

Luggage, shoes, shower curtains, carpets, mats, clothing and other useful household, public or industrial items are protected from rot, fungus stains and unsightly mold growth as well as infestation by mites by the active compounds of this invention. Again, either surface or deep protection can be obtained. Surface treatment is by dips, washes, sprays, aerosols or dust applications. Deep treatment is accomplished by penetrating solutions. Sprays, dips and washes contain the active compound of the invention at rates of 10 to 5000 parts per million. Fluids for aerosol application and dusts contain 0.1 to 20% by weight. Penetrating solvent solutions contain an amount of the active ingredient that results in a deposit of 5 to 20,000 parts per million in the material to be protected.

Painted surfaces can be protected from unsightly stain and mold growth by incorporating in the paint formulation, prior to application, 5 to 20,000 parts per million of an active compound of this invention. More preferred rates are in the range of 10 to 10,000 parts per million and the most preferred rates are in the range of 20 to 5,000 parts per million. Such treatments with the compounds of this invention also protect the paint while still in the can from deterioration by fungi.

In the case of certain products such as fiber board, paper woven materials, resinous and plastic parts, paints, etc., as described above, a compound of this invention can be incorporated into such articles during manufacture. For example, a slurry or solution can be added to the cellulose pulp during paper manufacture, or to the paint pre-mix prior to milling and dispersion.

Damage by mites to stored organic products such as grain, seed, bulbs, tubers, meat or animal hides is kept to a minimum by treating the floors, walls, portions, and other parts of warehouses or other structures with one or more of the active compounds. Applications are made by the use of dusts, sprays, or aerosols with preferred use rates in the range of 0.05 to 1000 grams of the active compound of this invention per 100 square meters of surface to be kept free of excessive mite populations.

The compounds of the invention are useful for controlling a wide variety of mite or fungus diseases of warmblooded animals.

Thus, for example, the compounds can be used to control the followng mites: *Dermanyssus gallinae* which attacks and can even kill domestic birds including chickens and pigeons and *Allodermanyssus sanguineus* which lives on rodents but can attack other animals.

The compounds are useful against many species of fungi, which include but are not limited to the following organisms: dimorphic fungi such as dermatitidis, immitis, capsulatum, compactum, pedrosoi, and schenckii; dermatophytes such as gypseum, and ouinii, gallinae, mentagrophytes and tonsurans; yeast-like fungi such as neoformans and other such as fumigatus and asteroides.

The compounds of this invention can be administered for fungicidial or mite-ovicidal effect according to this invention by any suitable means. For example, the compounds can be formulated as ointments, creams, pastes, external liquids, lotions, dusting powders, or aerosols and thus applied.

The dosage of compounds for this invention administered to the warm-blooded animal will depend upon the type of animal involved, the fungus involved, the frequency of administration and other factors known to those skilled in the art. Generally the fungus can be controlled by applying to the infected area a formulation containing in the range of from 0.025 to 95% by weight of a compound of the invention. A more preferred rate would be from 0.05 to 50% and the most preferred 0.1 to 25% by weight.

Besides the active ingredient of this invention, the formulation applied will contain a solid or liquid nontoxic pharmaceutical carrier for the active ingredient. When suitable sterile products are used, the compounds of the invention can be used for ophthalmic preparations, e.g., as ointments, external liquids, lotions, etc.

In one embodiment, the compound of the invention can be formulated as an ointment, cream or paste. In this formulation generally 0.01 to 10% by weight of the formulation is the active ingredient and the rest is a pharmaceutical base.

Examples of such bases are hydrophilic petrolatum, U.S.P.; hydrophilic ointment, U.S.P.; polyethylene glycol; and ointment, U.S.P. Other official bases or specially formulated bases as are common in the art can also be used.

These formulations are prepared by dissolving or suspending the active ingredient in the base, or a portion of the base, and passing the mix through an ointment mill.

In another embodiment, the active ingredient can be formulated as an external liquid. Generally this formulation will be 0.01 to 10% by weight active and the remainder a liquid carrier.

The liquid carrier can be aqueous, alcoholic or hydroalcoholic system, e.g., ethanol/water.

This formulation is prepared by dissolving the active in the solvent system, mixing and clarifying by filtration.

The compounds can also be formulated as lotions. The lotions will usually be 0.01 to 10% active and the rest a liquid phase. The liquid phase can be an aqueous system containing suitable wetting and suspending agents or it can be an emulsion of the O/W type, stabilized by suitable surface active agents.

The lotion can be prepared by triturating the active to a smooth paste and then cautiously adding the remaining liquid phase. High-speed mixers or homogenizers can be used to produce better dispersions.

The compounds can be formulated as dusting powders, generally with the compound being 0.01 to 10% of the formulation and the rest powder.

Talc, U.S.P. is the usual powder, although other powders common in the art can be used. The powder can also contain additive agents, such as magnesium stearate, to produce increased flowability.

Aerosol type packaging can be employed to provide a convenient method of dispensing the ointments, creams, pastes, liquids, lotions, or powders previously described. The aerosols are prepared using procedures common in the art.

The pressures of an expanding world population, together with the need for more economical agricultural pratices have resulted in earlier harvesting of grains, including corn. Frequently the grain is stored or sold to grain elevators without proper drying. Spoilage of the grain under these conditions may be quite rapid, with the formation of toxins and other substances that are very harmful or fatal when fed to animals.

Safe, effective feed additives that combat spoilage are thus of great importance to agriculture.

The compounds of this invention can be used to prevent the spoilage of animal feeds. In particular, when mixed with the feed, they provide more efficient and longer lasting protection without harm or injury to livestock that consume it. The compounds of this invention may be conveniently formulated for this use in a number of ways and these formulations may be mixed directly with mixed feed, newly harvested hay and newly harvested grain and oilseed. These compounds effectively prevent the spoilage of corn, sorghum, wheat, barley, oats, rye and other grains and oilseeds that may be used as livestock feed.

Under normal conditions, these compounds may be incorporated into feeds at rates of from 0.01% to 0.25% with excellent results. Higher rates may be required under very damp conditions.

These compounds can also be used to improve the performance of other feed additives, such as sodium propionate, by mixing the two additives directly, or by adding them separately to the feed to be protected.

As was previously set forth, the compounds of this invention are especially suited for use on living plants. Application to the foliage, stems and fruit of plants at the rate indicated above is generally accomplished by employing sprays, dusts or aerosols containing the proper amount of active ingredient. For the control of mites and fungi which are regularly present, applications often start prior to the time that the problem actually appears and continue on a pre-determined schedule. Such a procedure is termed "preventive" or "protective".

With the compounds of this invention, successful control of plant diseases can also be accomplished by applications made after they are present. Fungus mycelia within the plant tissue are actually killed. This approach or effect is termed "curative" or "eradicant" and permits the user to realize considerable savings.

Curative control of plant diseases with the compounds of this invention is enhanced if the treated plant parts are moist for one or more periods of 2 to 12 hours each soon after the active compound is applied. Often the slow drying of an original spray treatment or naturally occurring rains, mists, fogs or dews will accomplish this. Under other circumstances, such as during dry periods or in shelters such as greenhouses, it is necessary to keep the plants moist by some special effort for heat results.

The compounds of this invention have the added advantage that they have a high degree of stability. In some instances, benzimidazole derivatives have been known to degrade chemically with time, particularly under conditions of high humidity and temperature. The compounds of this invention are remarkably stable, and in this manner are easier to formulate and store.

Compositions

Compositions of this invention are formulated by mixing a compound of this invention with one or more surface-active agents or with a diluent carrier, or both.

The surface-active agents used in this invention can be wetting, dispersing or emulsifying agents. They may act as wetting agents for wettable powders and dusts, as dispersing agents for wettable powders and suspensions, and as emulsifying agents for emulsifiable concentrates. Surfactants also enhance the biological activity of the compounds of this invention. Such surface-active agents can include such anionic, cationic and nonionic agents as have heretofore been generally employed in plant control compositions of similar type. Suitable surface-active agents are set out, for example, in "Detergents and Emulsifiers Annual - 1968" by John W. McCutcheon, Inc. Other surface-active agents not listed by McCutcheon but still effective dispersants by virtue of protective colloid action include methylcellulose, polyvinyl alcohol, hydroxyethylcellulose, and alkyl-substituted polyvinyl pyrrolidones.

Suitable surface-active agents for use in compositions of this invention include polyethylene glycol esters with fatty and rosin acids; polyethylene glycol ethers with alkylphenols or with long-chain aliphatic alcohols; polyethylene glycol ethers with sorbitan fatty acid esters; and polyoxyethylenethioethers. Other suitable surfactants include amine, alkali and alkaline earth salts of alkyl aryl sulfonic acids, amine, alkali and alkaline earth fatty alcohol sulfates, dialkyl esters of alkali metal sulfosuccinates, fatty acid esters of amine, alkali and alkaline earth isethionates and taurates, amine, alkali and alkaline earth salts of lignin sulfonic acids, methylated or hydroxyethylated cellulose, polyvinyl alcohols, alkyl-substituted polyvinyl pyrrolidone, amine, alkali and alkaline earth salts of polymerized alkylnaphthalenesulfonic acids, and long-chain quaternary ammonium compounds. Anionic and nonionic surface-active agents are preferred.

Among preferred wetting agents are sodium alkylnaphthalene sulfonates, sodium dioctylsulfosuccinate, sodium dodecylbenzenesulfonate, ethylene oxide condensates with alkylated phenols such as octyl-, nonyl- and dodecylphenol, sodium lauryl sulfate, and trimethylnonyl polyethylene glycols. Among preferred dispersing agents are sodium, calcium and magnesium lignin sulfonates, low-viscosity methylcellulose, low-viscosity polyvinyl alcohol, alkylated polyvinylpyrrolidone, polymerized alkylnaphthalenesulfonates, sodium N-oleyl or N-lauryl isethionates, sodium N-methyl-N-palmitoyl taurate, and dodecylphenol polyethylene glycol esters.

Among preferred emulsifying agents are ethylene oxide adducts of lauric, oleic, palmitic or stearic acid esters of sorbitan or sorbitol, polyethylene glycol esters with lauric, oleic, palmitic, stearic or rosin acids; oil-soluble alkylarylsulfonates; oil-soluble polyoxyethylene ethers with octyl-, nonyl- and dodecylphenol, polyoxyethylene adducts to long-chain alcohols or mercaptans; and mixtures of these surfactants.

Compositions of this invention will contain, in addition to surface-active agents, solid or liquid diluents to produce wettable powders, dusts, granules or emulsifiable liquids as desired.

Wettable Powders

Wettable powders are compositions which usually contain inert solid diluents in addition to surfactants. These inert diluents may serve several purposes. They can act as grinding aids to prevent mill smear and screen blinding, they can aid rapid dispersion of the mix when placed in water, they can adsorb liquid or low-melting solid active material to produce a free-flowing solid product, they can prevent agglomeration into lumps upon prolonged hot storage, and they can permit preparation of compositions with a controlled amount of active ingredient so that proper dosage is easily measured by the consumer.

Suitable diluents may be either inorganic or organic in origin. These include the natural clays, diatomaceous earth, synthetic mineral fillers derived from silica or silicates, insoluble salts produced by precipitation in fluffy form such as tricalcium phosphate or calcium carbonate, and powdered organic diluents such as shell flours, wood flours, corn cob flour, sucrose, or pentaerythritol. Preferred fillers for the compositions of this invention include kaolin clays, attapulgite clay, non-swelling calcium magnesium montmorillonites, synthetic silicas, synthetic calcium and magnesium silicates, diatomaceous silica, corn cob flour and sugar.

Wettable powders will normally contain both a wetter and a dispersant. Most preferred for dry wettable powders are those anionic and nonionic surfactants which exist in solid form. Occasionally a liquid, nonionic surfactant, normally considered an emulsifying agent can be used to produce both wetting and dispersion.

Wetting and dispersing agents in wettable powders of this invention, when taken together, will comprise from about 0.5 weight percent to 5.0 weight percent of the total composition. The active component will be present at a concentration of from about 25 to 85%, and diluent makes up the balance to 100%. Where needed a corrosion inhibitor, foaming inhibitor, coloring agent, spray marker, or the like may be added at rates of 0.1 to 1.0% each, with a corresponding reduction in diluent.

The active compounds of this invention are highly potent fungicides that effectively control fungi when applied in conventional equipment as water dispersions in a concentration range of 200 to 600 ppm. However, because of improved methods of distribution of droplets and more economical operation it has become desirable to operate with 3 to 20 times the concentration formerly used in conventional equipment yet still apply the same quantity of active material per acre. These "Low-volume" or "Ultra-low-volume" concentrates are attainable with the wettable powders of this invention since little active material is required for control and low-viscosity concentrates are readily obtainable with relatively high solids content.

Dusts

Dust compositions are those intended for application in dry form with suitable dusting equipment. Since wind drift is undesirable when applying dusts, the most suitable dust diluents are those which are dense and rapid settling, These include kaolinites, talcs, pyrophyllites, ground phosphate rock, sulfur, Serecite, and ground tobacco stems. However, dusts are usually most easily prepared by diluting an existing high-strength wettable powder with a dense diluent so that the final dust will frequently contain a fraction of light, absorptive diluent as well as the more desirable dense filler.

A wetting agent is desirable in dust formulations so that adhesion to dew-covered foliage is enhanced. Dusts made from wettable powders will usually contain sufficient wetter, but dusts made directly from unformulated active will usually contain an added wetting agent. Dry solid anionic or nonionic wetters are preferred.

Dust formulations will normally contain from 2.0 weight percent to 25 weight percent of active material up from 0.005% to 1.0% wetting agent, and up to 20% light grinding aid diluent may be present. The balance will usually be dense, rapid settling diluent. If made by diluting a prepared wettable powder it will also contain a small amount of dispersing agent which has no active role when the composition is used as a dry dust.

Liquid Formulations

Emulsifiable liquids are formulated by combining the compounds of this invention with a suitable emulsifier and an organic liquid with low water-solubility. The active component may be completely dissolved in the organic liquid or it may be a finely ground suspension in a nonsolvent liquid. Suitable organic liquids include alkylated naphthalenes, xylene, high-molecular-weight ketones such as isophorones and dibutyl or diamyl ketone, esters such as amyl acetate, and normal or iso paraffins. Most preferred emulsifiers are blends of oil soluble sulfonates and nonionic polyoxyethylene glycol esters of fatty acids or ethers of fatty alcohols or alkylated phenols.

The active component in emulsifiable concentrates will be present at from 10 weight percent to about 40 weight percent. Combined emulsifiers will be present at from 3 weight percent to about 10 weight percent and the balance will be an organic carrier liquid or solvent.

Solvent solutions of active or dispersions of active solid in nonaqueous media offer the most practical compositions for "Low-volume" or "Ultra-low-volume" application from airborne or ground equipment. Formulated with emulsifiers, such mixes can be used as is or diluted to any desired degree with either water or oil. If only LV or ULV application is contemplated the emulsifier may, of course, be left out.

Granules

Soil treatments with fungicides, either pre- or post-emergence can frequently be most readily applied with granules. Granular products with the compounds of this invention can be made in a number of ways. The active materials can be melted or dissolved in a volatile carrier and sprayed upon preformed granules. They may be mixed as powders with suitable diluents and binders, then moistened and granulated followed by drying. Powders may also be applied to preformed granules by tumbling together and applying more binder such as nonvolatile oil or glycol, or a liquid nonionic surfactant, or a liqninsulfonate. Rates of granule disintegration and dispersion of active material in moist soil can be controlled by choice of added surfactants or selection of the binders used to form the granule.

Suitable preformed granules include those made from attapulgite clay, granular, expanded vermiculite, ground corn cobs, ground nut shells or preformed kaolinite granules. When active fungicide is placed upon such carriers the concentration may range from 1 to 25%. However, unless applied from a molten state, it is difficult to prevent segregation of active and carrier in concentration ranges above about 10% on preformed granules. When higher concentrations of active are desired best results are obtained by premixing powdered active, diluents, binders and surfactants and then granulating, so that the active is distributed throughout the granule and not solely upon its surface.

Suitable diluents for the preparation of granules by granulation or extrusion include carbohydrates, starches, sugar, kaolin clays, nonswelling Ca, Mg montmorrillonites, and gypsum. Cohesion to a firm granule is usually obtained by moistening compacting and drying, with or without some binding agent. Kaolin clays form firm granules if bound together with gelatinous agents such as methylcellulose, natural gums or swelling bentonite. Ca, Mg bentonites require no binder and gypsum can be made to form firm granules with either the addition of plaster of Paris or certain salts such as ammonium sulfate, potassium sulfate or urea which form double salts with gypsum.

The active content of formed granules can range from 1–90% although 75% active represents about the upper level if controlled disintegration of the granule in moist soil is desired. Control of disintegration rate is attained by controlled compaction, e.g. controlled extrusion pressure and by the addition of inert water soluble components such as sodium sulfate or surface-active agents which can leach away.

Aqueous Dispersions

Aqueous dispersions of fungicides are preferable to wettable powders where minimum agitation is available in application equipment and accurate dosage is essential. Even the best and finest wettable powder will not disperse completely in water. Small agglomerates remain which settle more rapidly. However, when a solid is ground in a water phase in the presence of dissolved surfactants, each particle develops an adsorbed layer that repels its neighbors, and complete dispersion is maintained. This will still not prevent a slow settling to the bottom of stored containers with the formation of a dense "clay" that is difficult to resuspend. A practical aqueous dispersion concentrate must be free from "claying" during an extended shelf life. Certain acrylic acid polymers and sheared hydrated attapulgite will effectively prevent claying.

Suitable aqueous dispersion of the compounds of this invention are prepared by pebble milling or sand milling the active ingredient, one or more dispersants and an anticlaying component in water until the active particle size is less than 10 microns, preferably less than 5 microns. In climates where freezing is a problem, antifreeze additives such as mixtures of glycols and water may be used as the continuous phase.

The compositions of the invention can contain, in addition to the active ingredient of this invention, conventional insecticides, miticides, bactericides, nematocides, fungicides, or other agricultural chemicals such as fruit set agents, fruit thinning compounds, fertilizer ingredients and the like, so that the compositions can serve useful purposes in addition to the control of fungi and mite infestations.

The following examples illustrate the activity of the compounds of Formula I. All parts are parts by weight unless otherwise indicated.

Wettable Powders

EXAMPLE 9

| | |
|---|---|
| Dimethyl 1,1'-(hexamethylenedicarbamoyl)-bis(2-benzimidazolecarbamate) | 50% |
| Sodium alkylnaphthalenesulfonate | 3% |
| Sodium N-methyl-N-palmitoyltaurate | 2% |
| Diatomaceous silica | 45% |

The above components are blended together and micropulverized followed by air-milling until substantially all particles are less than 5 microns.

The wettable powder thus prepared is added to water at the rate of 500 ppm of the active ingredient in water. This suspension is used to spray, to the point of run-off, alternate trees in a field planting of apples. Sprays are applied at weekly intervals from April 25 until June 6. From June 6 until the end of the season, the sprays are applied at intervals of two weeks. The remaining trees in the planting are left unsprayed.

In early September all trees are carefully examined. Trees that were sprayed with the compound of this invention are healthy and free of mite infestation and fungus damage. The fruit on the sprayed trees is unblemished and of good size. The foliage of the unsprayed trees, on the other hand, is heavily infested with the apple scab fungus (*Venturia inaequalis*) and the powdery mildew fungus (*Podosphaera leucotricha*). Also the leaves of the unsprayed plants are badly infested with European Red mites (*Panonychus ulmi*). The fruit on the unsprayed trees is spotted with scab and of small size.

EXAMPLE 10

| | |
|---|---|
| Dimethyl 1,1'-(2,2,4-trimethylhexamethylenedicarbamoyl)bis(2-benzimidazolecarbamate | 70% |
| Sodium lauryl sulfate | 2% |
| Alkyl-substituted polyvinylpyrrolidone | 0.5% |
| Chlorosilane-treated hydrophobic fine silica | 10% |
| Kaolin clay | 17.5% |

The above components are mixed, micropulverized and then air-milled in the same manner as described in Example 9.

Alternate rose bushes growing in a greenhouse are sprayed to runoff at weekly intervals with a suspension of the formulation described above. The concentration of active ingredient is 500 ppm in water containing 500 ppm of a wetting agent, a modified phthalic glycerol alkyl resin ("Triton" B 1956). After 2 months of this program the treated plants are healthy, with dark green attractive foliage and are growing well. The untreated plants, on the other hand, have much foliage discolored and curled due to infection by the rose powdery mildew fungus *Sphaerotheca humuli*. Other foliage on the untreated plants is yellowed due to attack by the Atlantic mite (*Tetranychus atlanticus*). Due to the extensive foliage damage, the plants not treated with the compound of this invention grow more slowly than the protected plants.

EXAMPLE 11

| | |
|---|---|
| Methyl 1,1'-{5-[2-(methozycarbonylamino)-1-benzimidazolylcarbonylamino]-1,3,3-trimethylcyclohexylmethylcarbamoyl}-2-benzimidazolecarbamate | 50 % |
| Sodium dioctyl sulfosuccinate | 3 % |
| Low-viscosity methylcellulose | 0.5% |
| Sucrose | 46.5% |

The above components are blended together and micropulverized, followed by air-milling until substantially all particles of the active ingredient are less than 5 microns.

Test plots are established in a rice field. The plots are sprayed with water containing a suspension of the wettable powder described above along with a polyhydric alcohol ester surface-active agent ("Trem" 014). The amount of the wettable powder used is such as to provide 1.5 grams of the active compound of this invention per liter of water. The amount of "Trem" 014 is 400 ppm in the final spray. The spray is applied at weekly intervals at the rate of 900 liters per hectare. The remainder of the field is left unsprayed. Three months after the start of the test, the sprayed plots are healthy and growing well. The untreated plots on the other hand, are seriously damaged by the rice blast fungus, *Piricularia oryzae*, which greatly reduces yield.

EXAMPLE 12

| | |
|---|---|
| Dimethyl 1,1'-(1,4-cyclohexylenedimethylenedicarbamoyl)bis(2-benzimidazolecarbamate) | 50% |
| Sodium lauryl sulfate | 3% |
| Oleic acid ester of sodium isethionate | 3% |
| Corn cob flour (minus 270 mesh) | 44% |

The above components are blended together and micropulverized until substantially all particles of active are less than 10 microns.

The formulation of this example is useful in controlling peach scab caused by the fungus *Cladosporium carpophilum*. This is demonstrated by a field study in which random trees in a peach planting are sprayed, starting in the spring, with water containing a suspension of the wettable powder above.

The amount of the wettable powder used is such as to provide 2.5 grams of the active compound of this invention per liter of water.

The spray is applied on a normal peach fungicide schedule at the rate of 2000 liters per hectare of peach trees. The remaining trees in the planting are left unsprayed.

At the time of harvest fruit on the treated trees are healthy and attractive to consumers. Conversely, fruit from the untreated trees is spotted with scab and of reduced market value.

EXAMPLE 13

| | |
|---|---|
| Dimethyl 1,1'-[methylenebis(1,4-cyclohexylene dicarbamoyl]bis(2-benzimidazolecarbamate) | 50% |
| Sodium alkylnaphthalenesulfonate | 3% |
| Alkyl-substituted polyvinylpyrrolidone | 2% |
| Anhydrous sodium sulfate | 45% |

The above components are blended, micropulverized and air-milled in the same manner as described in Example 9 to obtain particulate material consisting of particles that are less than 5 microns.

A uniform field planting of sugar beets in Ohio is selected. Alternate rows are sprayed with water containing a suspension of the wettable powder described above. The amount of the wettable powder used is such as to provide 300 ppm of the active compound of this invention. The spray is applied at weekly intervals at the rate of 1000 liters per hectare. The remaining rows are left unsprayed.

Twelve weeks after the initiation of the test, the sprayed rows of sugar beets are healthy and growing rapidly. The untreated rows, on the other hand, are heavily infected with the leaf spot fungus, *Cercospora beticola*. As a consequence of this fungus infection, the plants in the untreated rows are growing slowly and will clearly provide less yield.

EXAMPLE 14

| | |
|---|---|
| Diethyl 1,1'-(tetradecamethylenedicarbonyl)-dicarbamoyl)bis(2-benzimidazolecarbamate) | 10 % |
| Diamyl sodium sulfosuccinate | 0.5% |
| Pyrophyllite | 89.5% |

The active component, wetting agent and an equal weight of pyrophyllite are first blended, micropulverized and airmilled. The resulting powder is then blended with the balance of the pyrophyllite.

A uniform cherry orchard in Michigan is selected for the test. Alternate trees are dusted every 14 days at the rate of 900 grams per tree with the above dust formulation. The remaining trees are left unprotected.

On September 1 the trees are examined. The trees that had been dusted with the compound of this invention are green and healthy, with all leaves remaining on the trees. At this time the foliage of the unprotected trees is largely discolored due to attack by the leaf spot fungus (*Coccomyces hiemalis*) and the two spotted mite (*Tetranychus urticae*). Further, much of the foliage of the unprotected trees has fallen due to the effect of the two pests.

EXAMPLE 15

| | |
|---|---|
| Wettable powder of Example 10 | 7.15% |
| Ground tobacco stem dust | 92.85% |

The above components are blended together to give a 5% active dust.

Sugar cane seed pieces cut in November are divided into eight lots. Four of these lots are dusted in such a way as to cover all surfaces with the dust prepared as described above. The other four lots are dusted with the inert diluent only. All lots are stored under similar conditions until the following February at which time they are examined. The four lots that had been treated with the compound of this invention are in good condition. The four unprotected lots, on the contrary, are so badly rotted by fungi of the genus Fusarium that they cannot be planted.

EXAMPLE 16

| | |
|---|---|
| Diisopropyl 1,1'-[1,4-cyclohexylenedicarbonylbis(thiocarbamoyl)]bis(2-benzimidazolecarbamate) | 30% |
| Polyethylene oxide condensate with lauryl alcohol | 10% |
| Isoparaffin oil ("Soltrol" 170) | 60% |

The above components are mixed together then sandmilled until the active component is substantially all below 10 microns. The resulting oil suspension may be diluted with water to form a sprayable emulsion or it may be sprayed directly as a concentrate in suitable ultra-low volume spraying equipment.

The formulation of this example is useful in controlling Sigatoka disease of banana caused by the fungus *Cercospora musae*. This is demonstrated by a field test in which designated areas in a banana plantation are treated with 400 grams of the active ingredient of this invention per hectare applied in an amount of water sufficient to assure good distribution. The treatment is applied at intervals of 14 days.

Four months after the start of the test the banana plants in the treated plots are free from disease, whereas, the untreated plants are heavily damaged by Sigatoka disease.

EXAMPLE 17

| | |
|---|---|
| 50% Formulation of Example 9 | 10% |
| 30–60 Mesh granular vermiculite | 85% |
| Polyethyleneoxide condensate with nonylphenol | 5% |

The active formulation and vermiculite are blended briefly together, then sprayed with the surfactant followed by a second short blend. The surfactant acts as a binder to prevent segregation of active from the vermiculite yet aids liberation of active when the granules are placed in moist soil.

Four similar potted bean plants (one plant per pot) are selected. The soil in two of these pots is mixed with the granules of the formulation described above at a rate to provide 30 parts per million by weight of the active ingredient in the total amount of soil in the pot. The remaining two pots are left untreated.

Five days after treatment 50 adult mites (*Tetranychus urticae*) are placed on a terminal leaf on each of the best plants. Twenty-four hours later these adult mites, all still alive, are transferred to untreated bean foliage. After another 24 hours all of the adult mites are then removed in a way which causes no damage to the eggs that have been laid during the 24 hour period on the untreated foliage.

The number of eggs laid by each batch of 50 mites is essentially the same. A sufficient time is allowed for all viable eggs to hatch. Counts demonstrate that none of the eggs hatch from among those laid by mites that had fed on foliage from pots with soil containing the compound of this formulation. Hatch to provide living young was complete, on the other hand, among eggs laid by mites similarly handled except that the soil in the pot was untreated.

EXAMPLE 18

A latex house paint formulation contains the following ingredients:

| | Parts |
|---|---|
| Hydroxyethyl cellulose (2.5% solution) | 85 |
| Water | 68.5 |
| Nonionic dispersing agent: | |
| Tamol 731 (25%), sold by Rohm & Haas | 15 |
| Wetting agent: | |
| Triton CF-10, sold by Rohm & Haas | 2.5 |
| Antifoamer: | |
| Nopco NDW, sold by Nopco | 1 |
| Ethylene glycol | 25 |
| Non-chalking rutile titanium dioxide | 250 |
| Talc | 203.7 |
| Fungicide: | |
| dimethyl 1,1'-(4-methyl-m-phenylenedicarbamoyl)bis(2-benzimidazolecarbamate) | 1.2 |

The above materials are ground in a high-speed mill and let down, at a slower speed, as follows:

| | Parts |
|---|---|
| Acrylic resin: | |
| Rhoplex AC-388 (50%) | 459.8 |
| Antifoamer: | |
| Nopco NDW | 1 |
| Ammonium hydroxide (28%) ⎫ | 2 |
| Tributyl phosphate ⎬ Premix | 11.5 |
| Propylene glycol ⎭ | 35 |
| Water and/or hydroxyethyl cellulose (2.5%) | 17.5 |
| Toner: Cal/Ink GP8814E Phthalo Blue | 0.05 |
| Cal/Ink GP8807B Lamp Black | 0.05 |

Two coats of the latex paint was applied to Whatman No. 1 filter paper substrate. The first coat was allowed to dry for 24 hours before the second was applied. A 1½ inch square of the coated paper was subjected to heat (70°C.) for 24 hours followed by running tap water for 24 hours. The resulting paint chip is placed on the surface of malt agar in a petri plate and inoculated with an aqueous suspension of *Pullularia pullulans* (the predominant fungus isolated from mildew on painted surface). After a period of 4 weeks, the paint chip had completely inhibited the growth of the fungus whereas a second chip coated with paint containing no fungicide was completely covered with fungus.

Equal weights of the following compounds are substituted in the latex formulation for the dimethyl 1,1'-(4-methyl-m-phenylenedicarbamoyl)bis(2-benzimidazolecarbamate) above. The resulting paint films will be similarly effective in inhibiting the growth of fungi:

Dimethyl 1,1'-(p-phenylenedicarbamoyl)bis(2-benzimidazolecarbamate)
Dimethyl 1,1'-[methylenedi(p-phenylcarbamoyl)]bis(2-benzimidazolecarbamate)
Dimethyl 1,1'-[methylenebis(4-cyclohexylcarbamoyl)]bis(2-benzimidazolecarbamate)
Dimethyl 1,1'-(m-phenylenedicarbamoyl)bis(2-benzimidazolecarbamate
Dimethyl 1,1'-(2-methyl-m-phenylenedicarbamoyl)bis(2-benzimidazolecarbamate)

EXAMPLE 19

Example 18 is repeated using 0.12 part of the fungicide in place of the 1.2 parts. Paint chips prepared from the resulting formulation give similar results in inhibiting the growth of *Pullularia pullulans*.

EXAMPLE 20

Example 18 is repeated using 6 parts of the fungicide in place of the 1.2 parts. Paint chips prepared from the resulting formulation give similar results in inhibiting the growth of *Pullularia pullulans*.

EXAMPLE 21

An oil base house paint formulation containing the following ingredients is used in the following test.

|  | Parts |
|---|---|
| TI-PURE R-966 (Titanium dioxide) | 300 |
| Talc, stir-in grade | 315 |
| Long oil alkyd, "Dyal XAC-C129", sold by Sherwin-Williams Co. | 400 |
| 24% lead naphthenate | 6.9 |
| 6% manganese naphthenate | 1.4 |
| heavy mineral spirits | 169 |

To 1000 parts of the paint formulation described above is added 1 part of finely divided ( < 35 microns) dimethyl 1,1'-(4-methyl-m-phenylenedicarbamoyl)-bis(2-benzimidazolecarbamate).

A clapboard siding can be painted with one coat of the fungicidal oil base formulation, using an ordinary paint brush. After the paint film is allowed to dry, the clapboard will be resistant to fungal attack.

I claim:
1. A compound of the formula:

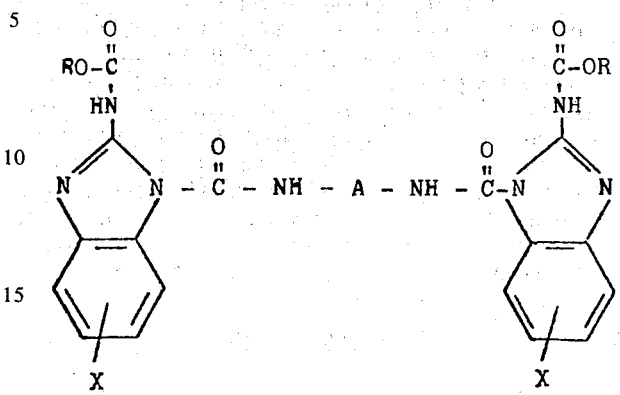

wherein
the R's can be the same or different and are methyl, ethyl, isopropyl or sec-butyl;
X is hydrogen, halogen, methyl or methoxy;
A is a difunctional group of 1 to 18 carbon atoms selected from
alkylene;
alkylene substituted by oxa, N-methylaza or thia;
alkenylene;
cycloalkylene;
cycloalkenylene;
bis(cyclohexylene)methylene;
alkylenated alkylcyclohexylene;
alkylated cyclohexylene;
alkylenated cyclohexylene;
bicycloalkylene;
phenylene;
methylated phenylene; and
bis(phenylene)methylene.

2. A compound of claim 1 wherein A is hydrocarbylene.

3. A compound of claim 1 wherein R is methyl and X is hydrogen.

4. Methyl 1-{5-[2-(methoxycarbonylamino)-1-benzimidazolylcarbonylamino]1,3,3-trimethylcyclohexylmethylcarbamoyl}-2-benzimidazolecarbamate.

5. Dimethyl 1,1'-(2,2,4-trimethylhexamethylenedicarbamoyl)bis(2-benzimidazolecarbamate).

6. Dimethyl 1,1'-(4-methyl-m-phenylenedicarbamoyl)bis(2-benzimidazolecarbamate).

* * * * *